United States Patent [19]

Macaudiere

[11] Patent Number: 5,755,868
[45] Date of Patent: May 26, 1998

[54] VERY FINELY DIVIDED RARE EARTH SULFIDE COLORANT COMPOSITIONS

[75] Inventor: Pierre Macaudiere, Asnieres/Seine, France

[73] Assignee: Rhone-Poulenc Chimie, Courbevoie Cedex, France

[21] Appl. No.: 874,903

[22] Filed: Jun. 16, 1997

Related U.S. Application Data

[63] Continuation of Ser. No. 436,725, May 8, 1995, abandoned.

[30] Foreign Application Priority Data

May 6, 1994 [FR] France .................................... 94 05588

[51] Int. Cl.$^6$ .................................................. C09C 1/02
[52] U.S. Cl. ................... 106/401; 106/400; 106/287.32; 106/286.2; 106/286.7; 423/263; 423/265; 423/266; 423/275; 423/561.1
[58] Field of Search ........................... 106/400, 401, 106/287.32, 286.2, 286.7; 426/263, 265, 266, 275, 561.1

[56] References Cited

U.S. PATENT DOCUMENTS

| | | | |
|---|---|---|---|
| 3,748,095 | 7/1973 | Henderson et al. | 423/21.1 |
| 4,619,792 | 10/1986 | Saunders et al. | 423/263 |
| 5,279,801 | 1/1994 | Colombet et al. | 423/21.1 |
| 5,348,581 | 9/1994 | Chopin et al. | 423/263 |
| 5,401,309 | 3/1995 | Chopin et al. | 423/263 |

FOREIGN PATENT DOCUMENTS

| | | |
|---|---|---|
| 203838 | 12/1986 | European Pat. Off. |
| 0545746 | 6/1993 | European Pat. Off. |
| 2126190 | 12/1971 | Germany . |

OTHER PUBLICATIONS

Materials Research Bulletin, vol. 19, No. 9, 1984, pp. 1215–1220, G. Adachi et al, Preparation & Structure of Soldium Rare–Earth Sulfides (no month).

*Primary Examiner*—Michael Marcheschi
*Attorney, Agent, or Firm*—Burns, Doane, Swecker & Mathis, L.L.P.

[57] ABSTRACT

Unique colorant compositions, well suited for the pigmentation of a wide variety of coatings and substrates, e.g., cosmetics, plastics, paints and rubbers, comprise (1) at least one crystalline rare earth metal sulfide or sesquisulfide, for example cubic cerium sesquisulfide $Ce_2S_3$, and (2) a dopant amount of at least one alkali metal, and wherein the at least one rare earth metal sulfide or sesquisulfide comprises whole (unground) monocrystalline grains thereof having a mean particle size of at most 1.5 μm.

17 Claims, No Drawings

VERY FINELY DIVIDED RARE EARTH SULFIDE COLORANT COMPOSITIONS

This application is a continuation of application Ser. No. 08/436,725, filed May 8, 1995 now abandoned.

BACKGROUND OF THE INVENTION

1. Technical Field of the Invention

The present invention relates to very finely divided colorant compositions based on rare earth metal sulfides and comprising at least one alkali metal, to a process for the preparation thereof and to the use of same for the improved pigmentation of a wide variety of materials and substrates.

2. Description of the Prior Art

Inorganic colorant pigments are today widely used in many industries, especially in those of paints, plastics and ceramics. For these applications, such properties as, inter alia, thermal and/or chemical stability, dispersibility (ability of the material to disperse properly in a given medium), intrinsic color, coloring capacity and opacifying power constitute particularly significant criteria to be considered in the selection of a suitable pigment.

Unfortunately, the problem remains that the majority of the inorganic pigments which are suitable for applications such as those indicated above and which are currently effectively used on an industrial scale generally comprise metals (cadmium, lead, chromium and cobalt especially), the use of which is becoming increasingly strictly controlled, indeed banned, by law in many countries because of their allegedly very high toxicity. More particularly exemplary are the red pigments based on cadmium selenide and/or cadmium sulfoselenide and for which substitutes based on the rare earth metal sulfides are already known to this art. Compositions based on rare earth metal sesquisulfides and alkali metal elements have thus been described, in EP-A-545,746. These compositions, which are obtained via a process comprising heating a mixture based on a rare earth metal compound, an alkali metal element and sulfur, have proven to be particularly advantageous substitutes.

However, need continues to exist for substitute materials having pigment-grade properties which are yet further improved and which can be prepared via an industrially even simpler process.

SUMMARY OF THE INVENTION

Accordingly, a major object of the present invention is the provision of improved colorant compositions which avoid or conspicuously ameliorate the above disadvantages and drawbacks to date characterizing the state of this art.

Briefly, the present invention features novel colorant compositions based on a rare earth metal sulfide and which comprise at least one alkali metal element, said metal sulfide comprising whole monocrystalline grains, the grains having a mean particle size of at most 1.5 μm.

This invention also features a process for the preparation of such novel colorant compositions based on a rare earth metal sulfide and at least one alkali metal, comprising contacting at least one rare earth metal carbonate or hydroxycarbonate with at least one compound of an alkali metal element and then heating the resulting admixture in the presence of at least one gas which comprises hydrogen sulfide or carbon disulfide.

DETAILED DESCRIPTION OF BEST MODE AND PREFERRED EMBODIMENTS OF THE INVENTION

More particularly according to the present invention, the subject colorants have an especially fine particle size, notably less than 2 μm, and very high coloration properties. The process for the preparation thereof is simple to carry out and, additionally, can be operated at relatively low temperatures, for example from about 500° C.

The colorant compositions of the invention will now be more fully described.

The subject colorant compositions are based essentially on at least one rare earth metal sulfide. Such at least one rare earth metal sulfide is very advantageously a sesquisulfide.

By "rare earth metal" are intended the elements belonging to the lanthanide group of the Periodic Table having an atomic number of from 57 to 71, as well as yttrium which has an atomic number of 39. By "Periodic Table" is intended that published in the Supplement to the Bulletin de la Société Chimique de France, No. 1 (January 1966). It will also be appreciated that the sulfide or the sesquisulfide of the compositions of the invention can comprise a number of rare earth metals and, thus, in the description that follows reference to a rare earth metal also applies to the case in which a number of rare earth metals are present.

This invention is particularly applicable to the sesquisulfides in which the rare earth metal is cerium or lanthanum.

The sulfide or the sesquisulfide of the compositions of the invention additionally comprises at least one alkali metal element (doping element, or dopant). This alkali metal element is especially selected from among lithium, sodium or potassium. Sodium is particularly preferred. Of course, the sulfide or sesquisulfide of the compositions of the invention can comprise a number of alkali metal elements and, again, reference to an alkali metal also applies to the case in which a number of alkali metals are present.

In a preferred embodiment of the invention, this alkali metal element is at least partially confined or enclosed within the crystalline lattice of the sulfide or sesquisulfide. In another embodiment, the alkali metal element is essentially or completely enclosed within the crystalline lattice.

The sesquisulfide of the compositions of the invention is, especially, a cubic crystallographic structure of $Th_3P_4$ type, which has gaps or voids in the cation lattice; this lacunary structure can be symbolized by according the sesquisulfides the formula $M_{10.66}[\ ]_{1.33}S_{16}$ (in this regard, see, in particular, W. H. Zachariasen, "Crystal Chemical Studies of the 5f-Series of Elements. The $Ce_2S_3Ce_3S_4$ Type of Structure", Acta Cryst., 2, 57 (1949)).

According to the invention, one or more alkali metal elements can be introduced into these cationic gaps, optionally up to saturation of the latter. The presence of this element within the sulfide or sesquisulfide can be demonstrated by simple chemical analysis. Moreover, X-ray diffraction analyses evidences that the $Th_2P_4$ crystalline phase of the sesquisulfide is retained with, in certain instances, modification of the unit cell parameters to a greater or lesser extent, depending both on the nature and on the amount of the doping element introduced.

Generally, the amount of alkali metal element is at most 50% of the molar amount of the rare earth metal in the sulfide or in the sesquisulfide.

In another preferred embodiment of the invention, the molar amount of alkali metal is at least equal to 0.1% and advantageously ranges from 5% to 50% and more preferably from 5% to 20% of the molar amount of rare earth metal.

An essential characteristic of the compositions of the invention is that they are based on a sulfide comprising whole monocrystalline grains, the grains having a mean particle size of at most 1.5 microns and preferably at most 1 micron. By "whole grain" is intended a grain which has not been broken or crushed. Grains can indeed be broken or crushed during milling. Scanning electron microscopy photographs of the product of the invention demonstrate that the grains of which it is comprised have not been crushed. It will also be appreciated that the sulfide or the sesquisulfide of the compositions of the invention can be deagglomerated, namely, if it is not provided directly in the form of whole monocrystalline grains, it can be provided in the form of agglomerates of particles which can comprise agglomerated and/or slightly sintered grains which can be converted, by deagglomeration under mild conditions, into the whole monocrystalline grains. The combination of the nature of the grain (whole particulates) and its small particle size is likely the explanation for the very good pigmentation properties of the composition of the invention.

The particulates of the invention, preferably have a mean particle size which is generally less than 2 µm and typically ranges from 0.7 to 1.5 µm. After deagglomeration under mild conditions, the mean particle size is at most 1.5 µm and advantageously ranges from 0.3 to 0.8 µm. The size of the particles is measured by Cilas particle size measurement.

The compositions based on sulfides or on sesquisulfides of the invention present a very wide range of colors depending especially on the rare earth metal and on the alkali metal element comprising the sulfides or sesquisulfides which indicates that their chromatic coordinates can vary over a very wide range. Exemplary thereof are the following:

(a) cerium sulfides have a color varying from brown to red depending on the preparation conditions, in particular the calcination temperature. They are brown or blood-red depending on whether the β-orthorhombic $Ce_2S_3$ phase or γ-cubic $Ce_2S_3$ phase is present;

(b) with lanthanum, yellow products are obtained having a cubic $La_2S_3$ structure;

(c) a green coloration is obtained with neodymium and a yellow/green coloration with praseodymium. The products then respectively have the cubic $Nd_2S_3$ structure and the cubic $Pr_2S_3$ structure;

(d) a brown/yellow product is obtained with dysprosium of cubic $Dy_2S_3$ structure;

(e) products having various shades of brown can also be obtained: ochre with terbium of cubic $Tb_2S_3$ structure, brown with erbium of monoclinic $Er_2S_3$ structure and dark beige with yttrium of monoclinic $Y_2S_3$ structure;

(f) lastly, other examples of colors which can be obtained are: grey/brown with samarium of cubic $Sm_2S_3$ structure, green/brown with gadolinium of γ-cubic $Gd_2S_3$ structure or gold/green with thulium of monoclinic $Tm_2S_3$ structure.

The process for the preparation of the compositions of the invention will now be more fully described.

A first characteristic of the subject process is nature of the starting materials. The rare earth metal is introduced in the form of a carbonate or of a hydroxycarbonate.

It is advantageous to use a carbonate or hydroxycarbonate having a fine particle size and, especially, having a mean particle size of at most 1 µm.

As regards the alkali metal element, it can be introduced in various forms. Exemplary thereof are the salts of these elements. However, it is advantageous to employ an alkali metal carbonate.

Preferably, a powder based on a homogeneous mixture of the rare earth metal carbonate or hydroxycarbonate with the compound of an alkali metal element is constituted.

In one embodiment of the invention, a rare earth metal carbonate or hydroxycarbonate is employed that has been impregnated beforehand with an alkali metal element. In this event, an aqueous solution of an alkali metal salt or hydroxide is formed and the rare earth metal carbonate or hydroxycarbonate is impregnated with this solution and then dried, according to any technique which limits the formation of oxide, for example in an oven, spray-drying, and the like.

Another characteristic of the process of the invention is the nature of the sulfurizing gas. This gas can be hydrogen sulfide or carbon disulfide. In a preferred embodiment of the invention, a mixture of these two gases is used. The use of such a mixture promotes the production of physically pure products and limits the deposition of carbon onto the product obtained. The sulfurizing gas or gas mixture can be used with an inert gas, such as argon or nitrogen.

The heating is carried out at a temperature which can be as low as 500° C. Indeed, the formation of the desired products has been observed at this temperature. This is a significant advantage with respect to known processes which require high temperatures, generally of at least 900° C. Typically, the process of the invention is carried out at a temperature ranging from 500° to 900° C., the higher temperatures promoting the production of phasically pure products.

The heating time corresponds to the time required to produce the desired sulfide or sesquisulfide and this time becomes shorter as the temperature becomes higher. For example, this time can range from approximately two hours for a temperature of 500° C. to approximately fifteen minutes for a temperature of 800° C.

The reaction is generally carried out employing a hydrogen sulfide and/or carbon disulfide partial pressure ranging from 0.1 to $1 \times 10^5$ Pa.

Lastly, the process can be carried out in an open reactor.

The product obtained on completion of the heating usually has a mean particle size of less than 2 µm and more particularly less than 1.5 µm. However, if it is desired to obtain a finer particle size, the product can be deagglomerated. As indicated above, a deagglomeration under mild conditions, for example using air-jet-type milling, is sufficient to obtain a mean particle size which can be less than 1.5 µm and, for example, at most 1 µm and advantageously ranging from 0.3 to 0.8 µm.

The present invention also features colored pigments comprising a composition based on at least one sulfide or sesquisulfide as described above, or produced via the subject process.

The compositions based on sulfides or on sesquisulfides or the pigments according to the invention have a very good coloration power and a very good covering or coating capacity. For this reason, they are perfectly suited for the coloration of a wide variety of substrates and materials, such as plastics, paints and others.

Thus, they are well suited for the coloration of plastics which can be of thermoplastic or thermosetting type.

Exemplary thermoplastic resins suited for coloration according to the invention include poly(vinyl chloride), poly(vinyl alcohol), polystyrene, styrene/butadiene, styrene/acrylonitrile or acrylonitrile/butadiene/styrene (A.B.S.) copolymers, acrylic polymers, especially poly(methyl methacrylate), polyolefins such as polyethylene, polypropylene, polybutene or polymethylpentene, cellulose derivatives such as, for example, cellulose acetate, cellulose acetobutyrate or ethyl cellulose, or polyamides, for example, polyamide-6,6.

Exemplary thermosetting resins for which the compositions or pigments according to the invention are also suitable include, for example, phenoplasts, aminoplasts, especially urea/formaldehyde or melamine/formaldehyde copolymers, epoxy resins and thermosetting polyesters.

The compositions or pigments of the invention can also be used for the coloration of special polymers such as fluorinated polymers, in particular polytetrafluoroethylene (P.T.F.E.), polycarbonates, silicone elastomers or polyimides.

In this specific application for the coloration of plastics, the compositions or pigments of the invention can be used directly in the form of powders. It is also possible, preferably, to employ the subject compositions in a predispersed form, for example a premix with a fraction of the resin, or in the form of a pasty concentrate, or of a liquid, permitting the compositions to be introduced at any stage in the manufacture of the resin.

Thus, the compositions or pigments according to the invention can be incorporated into plastics such as those indicated above in a proportion by weight generally ranging either from 0.01% to 5% (relative to the final product) or from 40% to 70% in the case of a concentrate.

The compositions or pigments of the invention can also be used in the field of paints and varnishes and, more particularly, in the following resins: alkyd resins, the most typical of which being referred to as glycerophthalic; resins modified with long or short chain oils; acrylic resins prepared from esters of acrylic (methyl or ethyl) and methacrylic acid optionally copolymerized with ethyl, 2-ethylhexyl or butyl acrylate; vinyl resins such as, for example, poly(vinyl acetate), poly(vinyl chloride), poly(vinyl butyral), poly(vinyl formal) and vinyl chloride and vinyl acetate or vinylidene chloride copolymers; aminoplastic or phenolic resins, most often modified; polyester resins; polyurethane resins; epoxy resins; or silicone resins.

Generally, the compositions or pigments are employed in a proportion of 5% to 30% by weight of the paint and of 0.1% to 5% by weight of the varnish.

Lastly, the compositions or pigments of this invention are also suitable for applications in the rubber industry, especially in floor coverings, in the paper and printing inks industry, in the field of cosmetics and in many other applications such as, for example, leather finishing and laminated coatings for kitchens and other work surfaces, or ceramics.

More particularly in respect of the cosmetics field, the compositions or pigments of the invention are useful in nail varnishes and in makeup products such as lipsticks, dry makeups, greasy makeups or foundation creams.

They can thus be formulated into nail varnishes and polishes which generally contain:

(a) a film-forming agent based on nitrocellulose,
(b) a resin, natural dammar resin or synthetic resin of formaldehyde/sulfamide type, polystyrene resin, polyvinyl resin, and the like.
(c) a plasticizer, for example diethyl phthalate, dibutyl phthalate, dioctyl phthalate, tricresyl phosphate, n-butyl stearate, resorcinol diacetate or mixture thereof,
(d) a solvent such as ethyl, isopropyl, butyl or isobutyl alcohol, ethyl acetate, butyl acetate or, typically, a mixture of these solvents,
(e) a diluent, especially toluene or xylene,
(f) optionally, other additives and adjuvants, fragrances or pearlessence compounds (mica flakes coated with bismuth oxychloride or titanium dioxide).

An exemplary such composition is given below:
(i) from 10% to 15% by weight of nitrocellulose,
(ii) from 10% to 15% by weight of resin,
(iii) from 3% to 5% by weight of plasticizer(s),
(iv) from 3% to 5% by weight of pigment(s),
(v) q.s. for 100% by weight of solvent(s).

Generally, the compositions or pigments are milled in a plastic mass comprising nitrocellulose and plasticizer(s), which is then dissolved in the solvent(s).

Another application of the compositions or pigments of the invention is for formulation into lipsticks.

The compositions or pigments are most typically incorporated in a proportion of a concentration by weight of 5% to 15% expressed with respect to the total weight of the formulation which contains:

(a) an excipient formed from a mixture of various materials to provide for consistency: beeswax, carnauba wax, ozocerites, paraffin, synthetic waxes or mixture thereof and from a soft excipient which permits adjusting the consistency, such as cocoa butter, petroleum jelly, hydrogenated white oils for example, or palm, groundnut or castor oil.
(b) various additives and adjuvants, especially a fragrance or flavor and isopropyl myristate or isopropyl palmitate which provides slipperiness.
(c) an intermediate solvent for suspending the pigment in the lipophilic phase, which can be castor oil or a glycol, such as polyethylene glycol 400, or fatty acid esters: propylene glycol monoricinoleate, isopropyl myristate, isopropyl palmitate or butyl stearate.

The eye shadows and blushes can be provided in the form of dry makeup products or greasy makeup products. The content of the subject compositions or pigments in such makeups can vary over wide limits, for example from 5% to 20%.

The dry makeup products are powders (talc, magnesium carbonate or zinc stearate) which are laden with pigments and agglomerated either with methyl cellulose or with stearates.

The following is an exemplary composition for an eye shadow:

| | |
|---|---|
| (i) aluminum magnesium silicate (Veegum F): | 7% by weight |
| (ii) talc: | 50% by weight |
| (iii) zinc oxide: | 4% by weight |
| (iv) zinc stearate: | 11% by weight |
| (v) kaolin: | 10% by weight |
| (vi) pigment: | 18% by weight |

The compositions or pigments of the invention can also be incorporated in foundation cream formulations.

The foundation creams are provided in the form of an emulsion, characteristically of the oil-in-water type.

The lipophilic phase typically comprises:

(a) an oily component such as liquid paraffin, esters of fatty acids and of optionally fatty alcohols, for example oleyl oleate, decyl oleate, octyl stearate, di-n-butyl adipate, isopropyl myristate, isopropyl palmitate, isopropyl stearate or the esters of capric and caprylic acids with saturated fatty alcohols having from 12 to 18 carbon atoms, a silicone oil or mixture thereof,
(b) an emulsifying agent of anionic and/or nonionic type and, especially, the salts of fatty acids, sodium, potassium or ammonium stearate or sodium palmitate: the esters of sorbitan and of fatty acids such as, for example, lauric acid, palmitic acid or stearic acid; the polyoxyethylenated esters of sorbitan and of fatty acids containing from 4 to 20 mol of ethylene oxide per mole of ester: the polyoxyethylenated fatty alcohols containing from 2 to 23 mol of ethylene oxide per mole of alcohol, said alcohol especially being lauryl alcohol, cetyl alcohol, stearyl alcohol or oleyl alcohol; glyceryl mono- and distearate or glyceryl mono- and dioleate; polyoxyethylenated fatty acids and in particular polyoxyethylenated stearate containing from 18 to 100 mol of ethylene oxide per mole of acid.

(c) an agent for adjusting the consistency of the product, which advantageously is a fatty alcohol or a fatty acid and more particularly cetyl alcohol, stearyl alcohol or stearic acid.

With respect to the hydrophilic phase, it comprises water, preferably distilled, and various additives and adjuvants, especially:

(a) a humectant which can be, for example, propylene glycol, glycerol or sorbitol.

(b) a preservative and more particularly o-phenylphenol and the following acids, their salts (Na, K or $NH_4$) or their esters having from 1 to 4 carbon atoms: benzoic acid, salicylic acid, sorbic acid or p-hydroxybenzoic acid.

(c) a stabilizing agent, especially cellulose derivatives including carboxymethyl cellulose and xanthan gum.

An exemplary formulation for a foundation cream is as follows:

| (A) Lipophilic phase: | |
|---|---|
| (i) liquid paraffin: | 15% by weight |
| (ii) glyceryl mono- and distearate: | 4% by weight |
| (iii) cetyl alcohol: | 1% by weight |
| (B) Hydrophilic phase: | |
| (i) distilled water q.s. for: | 100% by weight |
| (ii) propylene glycol: | 3% by weight |
| (iii) methyl para-hydroxybenzoate: | 0.05% by weight |
| (iv) propyl para-hydroxybenzoate: | 0.1% by weight |
| (v) colorant pigment: | 1 to 10% by weight |
| (vi) titanium dioxide: | 3% by weight |

The preparation of the foundation cream formulations is carried out by first dispersing the pigment in the lipophilic phase, maintained at a temperature of about 60°–80° C. and then adding the hydrophilic phase, maintained at a temperature within the above range, with stirring and slowly to the lipophilic phase.

In the foregoing description, the reported formulations for cosmetics comprising the compositions or pigments of the invention are exemplary only.

The present invention also features the compositions, substrates and shaped articles comprising the subject colorants. Such compositions, substrates and shaped articles include plastics, paints, varnishes, rubber, ceramics, glazings, papers, inks, cosmetics, dyes, laminated coatings, and the like.

In order to further illustrate the present invention and the advantages thereof, the following specific examples are given, it being understood that same are intended only as illustrative and in nowise limitative.

In said examples to follow, the chromatic coordinates $L^*$, $a^*$ and $b^*$ are reported in the CIE system 1976 ($L^*$, $a^*$, $b^*$) as defined by the International Lighting Commission and catalogued in the Compilation of French Standards (AFNOR), calorimetric color No. X08-12 (1983). They are determined using a calorimeter marketed by Pacific Scientific. The illuminant was D65. The observation surface was a circular pellet having a surface area of 12.5 cm$^2$. The observation conditions correspond to viewing at an aperture angle of 10°. The specular component was excluded from the measurement reported.

$L^*$ is a measurement of the reflectance (light/dark shading) and thus ranges from 100 (white) to 0 (black).

$a^*$ and $b^*$ are the values of the color trends:

$a^*$ positive=red $a^*$ negative=green $b^*$ positive=yellow $b^*$ negative=blue $L^*$ thus represents the variation from black to white, $a^*$ the variation from green to red and $b^*$ the variation from yellow to blue.

EXAMPLE 1

This example relates to the preparation of a cubic cerium sesquisulfide comprising sodium values.

6 g of cerium hydroxycarbonate, having a Cilas particle size less than 1 µm, and 0.22 g of anhydrous sodium carbonate were introduced into a mortar. The Na/Ce molar ratio was then 0.2.

The entire mixture was then ground to provide a homogeneous mixture. This mixture was then heated to 500° C. for 2 hours, while continuously sweeping the reaction zone with a gas mixture containing argon, hydrogen sulfide and carbon disulfide (50%, 20% and 30% respectively by volume).

The product thus obtained was principally cubic cerium sesquisulfide, as determined by X-ray diffraction analysis. Its particle size was less than 1 µm.

EXAMPLE 2

A cubic cerium sesquisulfide doped with lithium was prepared by calcining a mixture of cerium hydroxycarbonate, of the same type as that in Example 1, and lithium carbonate at a constant temperature of 800° C. for 90 minutes under an atmosphere containing carbon disulfide, in the proportion of a partial pressure of $0.3 \times 10^5$ Pa, and hydrogen sulfide, in the proportion of $0.2 \times 10^5$ Pa, in argon. The Li/Ce molar ratio in the mixture was 0.10.

The product obtained was a red pigment whose color coordinates and particle size were the following:

$L^*=45.1$ $a^*=46.1$ $b^*=34.1$ $D_{50}=1.5$ µm

After simple deagglomeration, the product obtained was in the form of whole monocrystalline grains having a particle size of less than one micron. The $D_{50}$ of the product was 0.65 µm.

EXAMPLE 3

In contradistinction to the above examples, the alkali metal was uniformly distributed in the rare earth metal precursor by impregnation of said precursor with the alkali metal salt (sodium carbonate) in solution. The alkali metal was here present in an Na/Ce ratio of 0.15. After treatment with a sulfurizing mixture containing 30% (by volume) of $CS_2$, 20% of hydrogen sulfide and the remainder as argon, at a constant temperature of 800° C. for 30 minutes, the sesquisulfide was crystallized in the $Th_3P_4$ structure.

Its color characteristics were the following:

$L^*=55.9$ $a^*=50.3$ $b^*=43.3$ $D_{50}=1$ µm

After deagglomeration, the product obtained had a $D_{50}$ of 0.65 µm and whole monocrystalline grains having a particle size of less than one micron.

EXAMPLE 4

This example describes the synthesis of a cerium sulfide having a very small particle size.

Under a partial pressure of $0.3 \times 10^5$ Pa of $CS_2$, $0.2 \times 10^5$ Pa of $H_2S$ and the remainder as argon, a cerium carbonate having a Cilas particle size of 0.7 µm was converted, in the presence of sodium carbonate in an Na/Ce ratio of 0.15, into cubic cerium sulfide, at a constant temperature of 800° C. for 30 min. It had the following color characteristics and particle size:

$L^* = 55.6$
$a^* = 46.2$
$b^* = 45.1$
$D_{50} = 0.9$ µm

After simple deagglomeration, the mean diameter was 0.55 µm. The product was in the form of whole monocrystalline grains having a particle size of less than one micron.

EXAMPLE 5

In contradistinction to the above examples, a mixture containing only carbon disulfide as the sulfurizing agent, diluted to 30% in argon, was employed. 6 g of cerium hydroxycarbonate were mixed with 0.29 g of sodium carbonate and the mixture was heated to 800° C. for 5 h. A product was obtained which was divided into two fractions according to a color criterion. The X-ray analyses evidenced, indeed, a pure cubic phase for a red fraction and a cubic phase, as well as a brown oxysulfide phase, for the second fraction.

The color coordinates of the reddest fraction were the following:

$L^* = 49.8$
$a^* = 48.8$
$b^* = 40.2$
$D_{50} = 2.0$ µm

After deagglomeration, the mean diameter of the particulates was 1.45 µm.

Sulfurization in the presence of carbon disulfide and hydrogen sulfide (30% and 20% by volume, the remainder as argon) of the same cerium hydroxycarbonate produced a single cubic cerium sesquisulfide phase whose chromatic coordinates were the following:

$L^* = 50.7$
$a^* = 51.5$
$b^* = 42.1$

The product was in the form of whole monocrystalline grains having a particle size of less than one micron.

EXAMPLE 6

A cerium hydroxycarbonate having a particle size of less than 1 µm was mixed with a sodium carbonate in the proportion of an Na/Ce ratio=0.15. This mixture, heated to a constant temperature of 750° C. for 2 h, under a sulfurizing atmosphere of $CS_2$, $H_2S$ and argon (30%, 20% and 50%, respectively, by volume), produced a cerium sulfide of $Th_3P_4$ type whose color coordinates were the following:

$L^* = 52.2$
$a^* = 50.4$
$b^* = 46.7$
$D_{50} = 1.4$ µm

After deagglomeration, the mean diameter was 0.8 µm. The product was in the form of whole monocrystalline grains having a particle size of less than one micron.

EXAMPLE 7

In this example, the synthesis was carried out of a pigment, employing a very short thermal cycle: 9 g of a cerium hydroxycarbonate having a particle size of less than 1 µm, mixed with 0.31 g of sodium carbonate, were heated at a temperature of 800° C. for 15 min in the presence of a mixture of argon, hydrogen sulfide and carbon disulfide at, respectively, 50%, 20% and 30% by volume. The chromatic coordinates of the final product were the following:

$L^* = 51.3$
$a^* = 50$
$b^* = 42.6$
$D_{50} = 1.5$ µm

The product was in the form of whole monocrystalline grains having a particle size of less than one micron.

EXAMPLE 8

This example relates to the preparation of a mixed cerium lanthanum sulfide.

A cerium lanthanum hydroxycarbonate having a Ce/La molar ratio of 3 and having a particle size of less than one micron was sulfurized at a constant temperature of 800° C. for 30 minutes in the presence of sodium carbonate in a proportion of 20 molar % with respect to the rare earth metals. The sulfurizing gas was a mixture of carbon disulfide, hydrogen sulfide and argon in the respective proportions of 30%, 20% and 50% by volume. The color and particle size characteristics thereof were the following:

$L^* = 56.3$
$a^* = 50.7$
$b^* = 48.9$
$D_{50} = 1.7$ µm

After deagglomeration, the mixed sesquisulfide had a mean size of 0.85 µm. The product was in the form of whole monocrystalline grains having a particle size of less than one micron.

EXAMPLE 9

A praseodymium sulfide was prepared by reacting a gas mixture containing 30% by volume of carbon disulfide and 15% of hydrogen sulfide, the remainder to 100 being contributed by argon, with a mixture of praseodymium carbonate and sodium carbonate (Na/P ratio of 0.2). The temperature of the synthesis was 800° C. and the constant temperature period was 5 hours.

The sesquisulfide obtained had a particle size of less than one micron and its chromatic coordinates were the following:

$L^* = 86.9$
$a^* = -15.2$
$b^* = 57.8$

The product was in the form of whole monocrystalline grains having a particle size of less than one micron.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A colorant composition of matter which comprises (1) at least one crystalline rare earth metal sulfide or sesquisulfide and (2) a dopant amount of at least one alkali metal, said at least one rare earth metal sulfide or sesquisulfide comprising grains thereof having a mean particle size of at most 1.5 μm wherein said grains are whole monocrystaline grains.

2. The colorant composition as defined by claim 1, wherein at least a fraction of said at least one alkali metal being included within a crystal lattice of said at least one rare earth metal sulfide or sesquisulfide.

3. The colorant composition as defined by claim 2, said at least one alkali metal being included in cation gaps within the crystal lattice of said at least one rare earth metal sulfide or sesquisulfide.

4. The colorant composition as defined by claim 1, having a molar amount of said at least one alkali metal of at most 50% of the molar amount of the at least one rare earth metal.

5. The colorant composition as defined by claim 4, the molar amount of said at least one alkali metal ranging from 5% to 50% of the molar amount of the at least one rare earth metal.

6. The colorant composition as defined by claim 1, wherein said at least one alkali metal comprises sodium.

7. The colorant composition as defined by claim 1, wherein said at least one rare earth metal sulfide or sesquisulfide has a $Th_3P_4$ crystallographic structure.

8. The colorant composition as defined by claim 1, wherein said at least one rare earth metal sulfide or sesquisulfide comprises γ-cubic cerium sesquisulfide $Ce_2S_3$.

9. The colorant composition as defined by claim 1, wherein said at least one rare earth metal sulfide or sesquisulfide comprises cubic lanthanum sesquisulfide $La_2S_3$.

10. A process for the preparation of the colorant composition as defined by claim 1, comprising mixing a carbonate or hydroxycarbonate of at least one rare earth metal with at least one alkali metal compound to form a mixture, heating the mixture thus produced in the presence of at least one gas which comprises hydrogen sulfide, carbon disulfide, or mixture thereof to form a product, and, optionally, deagglomerating the product.

11. The process as defined by claim 10, wherein said at least one gas comprises a mixture of hydrogen sulfide and carbon disulfide.

12. The process as defined by claim 10, said at least one alkali metal compound comprising an alkali metal carbonate.

13. The process as defined by claim 10, said carbonate or hydroxycarbonate of at least one rare earth metal having been impregnated with at least one alkali metal.

14. The process as defined by claim 10, carried out in an open reactor.

15. The process as defined by claim 10, wherein the hydrogen sulfide and/or carbon disulfide has a partial pressure of from 0.1 to $1\times10^5$ Pa.

16. A colorant composition of matter which comprises (1) at least one crystalline rare earth metal sulfide or sesquisulfide and (2) a dopant amount of at least one alkali metal, said at least one rare earth metal sulfide or sesquisulfide being in the form of agglomerates which comprise agglomerated grains having a mean particle size of at most 1.5 μm wherein said grains are whole monocrystalline grains.

17. The colorant composition of matter as defined by claim 1, wherein said grains have a mean particle size of between 0.3 and 0.8 μm.

* * * * *